(12) United States Patent
Angelsen et al.

(10) Patent No.: US 6,780,153 B2
(45) Date of Patent: Aug. 24, 2004

(54) MECHANISM AND SYSTEM FOR 3-DIMENSIONAL SCANNING OF AN ULTRASOUND BEAM

(76) Inventors: Bjørn A. J. Angelsen, Bugges veg 4b, 7051 Trondheim (NO); Tonni F. Johansen, Osloveien 6, 7018 Trondheim (NO); Stig B. Kjøde, Loholtbakken 1a, 7049 Trondheim (NO)

( * ) Notice: Subject to any disclaimer, the term of this patent is extended or adjusted under 35 U.S.C. 154(b) by 0 days.

(21) Appl. No.: 10/179,160

(22) Filed: Jun. 24, 2002

(65) Prior Publication Data
US 2003/0018269 A1 Jan. 23, 2003

Related U.S. Application Data
(60) Provisional application No. 60/300,788, filed on Jun. 25, 2001.

(51) Int. Cl.$^7$ ................................................. A61B 8/00
(52) U.S. Cl. ............................................. 600/444
(58) Field of Search ............................... 600/443–449, 600/459; 73/631–632; 128/916

(56) References Cited

U.S. PATENT DOCUMENTS

| | | | |
|---|---|---|---|
| 3,690,311 A | * 9/1972 | Schorum et al. | 600/444 |
| 4,233,988 A | * 11/1980 | Dick et al. | 600/443 |
| 4,271,706 A | * 6/1981 | Ledley | 73/614 |
| 4,398,425 A | 8/1983 | Matzuk | |
| 4,399,703 A | 8/1983 | Matzuk | |
| 4,479,388 A | * 10/1984 | Matzuk | 73/634 |
| 4,579,122 A | 4/1986 | Shimizu et al. | |
| 4,757,823 A | * 7/1988 | Hofmeister et al. | 600/459 |
| 4,762,002 A | * 8/1988 | Adams | 73/625 |
| 4,787,247 A | * 11/1988 | Wuchinich et al. | 73/620 |
| 4,841,979 A | * 6/1989 | Dow et al. | 600/446 |
| 5,088,495 A | * 2/1992 | Miyagawa | 600/446 |
| 5,094,243 A | 3/1992 | Puy et al. | |
| 5,152,294 A | * 10/1992 | Mochizuki et al. | 600/459 |
| 5,159,931 A | * 11/1992 | Pini | 600/443 |
| 5,460,179 A | * 10/1995 | Okunuki et al. | 600/447 |
| 6,245,020 B1 | * 6/2001 | Moore et al. | 600/466 |

* cited by examiner

Primary Examiner—Francis J. Jaworski
(74) Attorney, Agent, or Firm—Cohen, Pontani, Lieberman & Pavane

(57) ABSTRACT

An ultrasound probe capable of scanning an ultrasound beam in a region of 3D space, characterized by that an ultrasound transducer array is mounted to a $1^{st}$ shaft that can rotate in bearings mounted in a fork that can be moved. The fork can be rotated around a $2^{nd}$ shaft in a bearing, or moved through a sliding system, or a combination of the two. The shaft and the fork are connected to two separate electric motors for electric steering of the array direction within a region of 3D space. Position measurement systems are mounted to the shaft and the fork so that the beam direction can be steered with a feed-back control system.

15 Claims, 6 Drawing Sheets

MECHANISM AND SYSTEM FOR 3-DIMENSIONAL SCANNING OF AN ULTRASOUND BEAM

CLAIM OF DOMESTIC PRIORITY

The applicants hereby claim domestic priority from prior-filed provisional application Ser. No. 60/300,788, filed Jun. 25, 2001.

BACKGROUND OF THE INVENTION

1. Field of the Invention

The present invention is directed to technology and methods for scanning an ultrasound beam in a free direction within a region of 3D space. The technology has particular applications within 3D medical ultrasound imaging, but also has applications in other areas of ultrasound imaging or other areas where mechanical movement of an object in 3D space is required.

2. Description of the Related Art

Three-dimensional (3D) ultrasound imaging of biological structures can be done by scanning a pulsed ultrasound beam in a 3D manner, and recording the back-scattered ultrasound signal in each beam direction. The principle was described already in the 50'ies, and several instruments have been built that applies the method.

With 3D imaging, it is important that the ultrasound beam is maximally focused, symmetrically in all directions around the beam axis, as one wants to observe the object from any direction (perspective), and small objects can be interrogated with a variety of beam directions. Such symmetric focusing can be obtained by subdividing the elements of a linear transducer array in the elevation direction, i.e. the direction normal to the two-dimensional (2D) scan plane. The 2D scan plane is often referred to as the azimuth scan plane, while the direction normal to the 2D scan plane is referred to as the elevation direction. Linear arrays with subdivision of the elements in the elevation direction are referred to as 1.5D or 1.75D arrays, depending on whether the elements can be symmetrically or individually steered around the azimuth mid plane. A problem with the subdivision of the elements is that the size of the elements are reduced, increasing the element impedance and hence also noise. The subdivision also gives a large total number of elements, leading to a large number of wires between the array elements and the electronic beam former. This increases cable losses and hence sensitivity of the array.

Symmetric focusing of the beam can be obtained with much fewer and larger elements with an array of concentric annular elements, the so-called annular array. The larger elements provide lower element impedances and hence less noise and cable losses. Another advantage with the annular array, is that it is covered in a dome, so that the array itself is not pushed against the body or other objects as the linear arrays typically are done. This allows the use of materials with lower characteristic impedance for mechanical backing support with the annular array compared to the linear arrays, giving less acoustic backing losses and hence better sensitivity with the annular array.

Hence the annular array provides better sensitivity for symmetrical focusing of the beam around the beam axis than the linear arrays, due to the large elements and low impedance backing material. The increased sensitivity in turn allows the use of higher ultrasound frequencies and hence better resolution for a given depth, than the linear arrays. The low number of elements also reduces the number of connecting cables and hence gives a lower manufacturing cost of the array.

A problem with the annular array for 3D beam scanning, is that scanning of the beam direction requires mechanical movement of the array. 3D scanning of the beam with small size of the whole scanning mechanism is then difficult, and the present invention provides a solution to this problem. With a particular embodiment of the invention, the annular array beam can be scanned in a 3D sector with more than 200 deg opening angle in both the elevation and the azimuth directions, with a dimension of the scan-head only slightly larger than the active radiation aperture of the array. The narrow head and wide scanning angle provide a probe that is small and easy to handle, and has special advantages for endoluminal and surgical imaging, where the probe is placed in narrow channels with limited possibilities to direction steer the probe, like for example with transvaginal, transrectal, transesophageal, transgastric, and transintestinal imaging, and imaging from narrow surgical wounds.

BRIEF DESCRIPTION OF THE DRAWINGS

In the drawings:

FIG. 1a shows sliding of the fork in a sliding system that provides rotation of the array around an elevation axis normal and close to the azimuth axis;

DETAILED DESCRIPTION OF THE PRESENTLY PREFERRED EMBODIMENTS

Figure 1A:
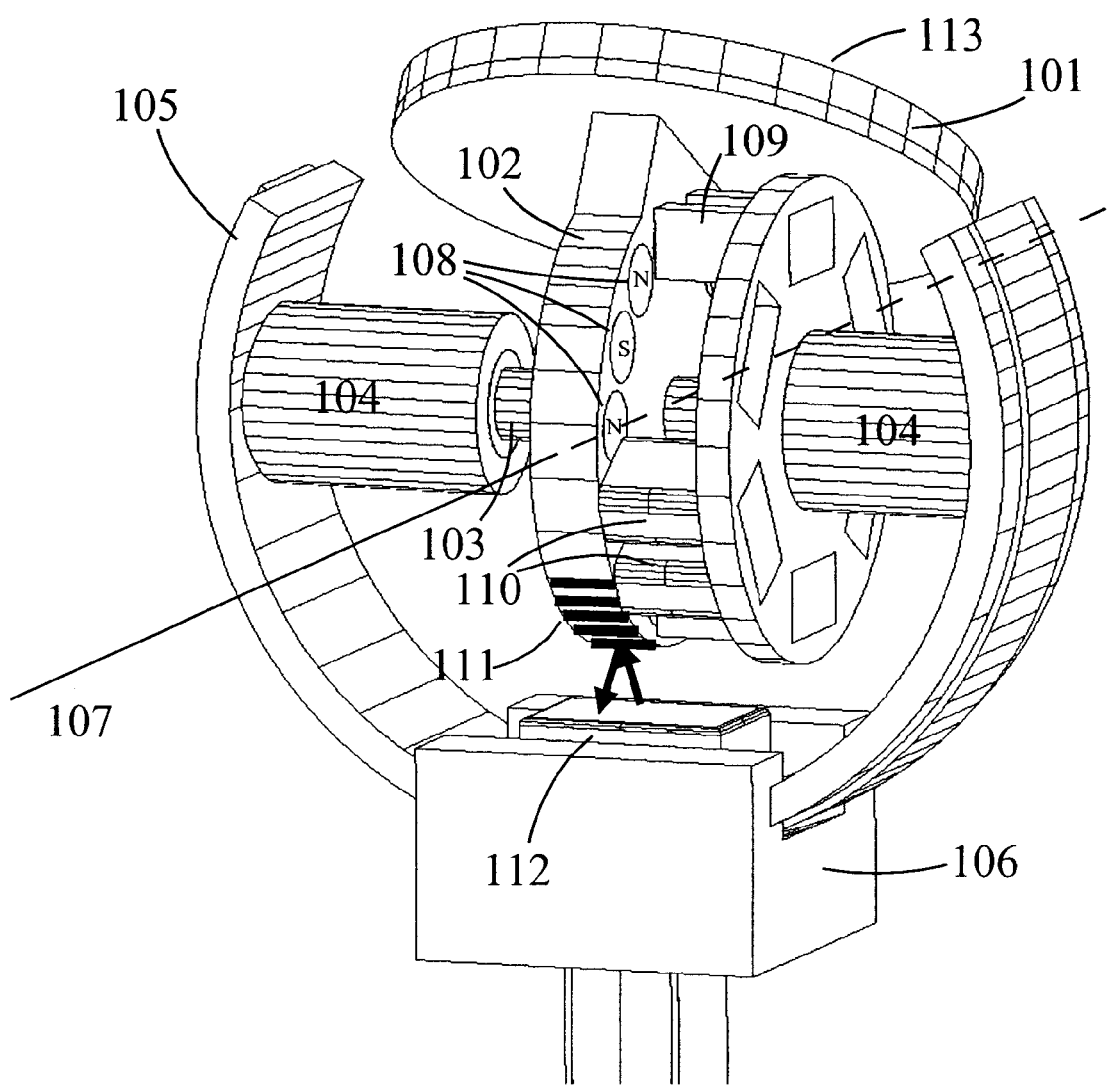
FIG. 1a shows particular embodiments according to the invention that provides rotation of a transducer or transducer array around an azimuth axis defined by a $1^{st}$ shaft that rotates in bearings mounted in a fork that can be moved, where

A particular embodiment of the invention will be described with reference to the drawings. In FIG. 1a 101 shows an annular array that is attached to the rotor 102 of an electric motor that is attached to a shaft 103 that is free to move in bearings 104 mounted in a fork 105. Rotating the array around the shaft 103 scans the ultrasound beam in an angular direction referred to as the azimuth direction, within a 2D plane referred to as the azimuth plane. The fork 105 is mounted in a sliding system 106 which allows movement of the shaft. In this particular embodiment, the fork has a circular shape so that sliding of the fork through the sliding system produces a rotation of the shaft 103 around an axis 107, normal to the shaft, which allows angular scanning of the beam in what is referred to as the elevation direction. Moreover, this particular embodiment produces a rotation of the shaft around an axis on the same side of the sliding system as the shaft itself, and the axis 107 goes through the center of the shaft 103. This embodiment allows for a compact size of the mechanism in relation to the size of radiating acoustic surface aperture 113 of the transducer array 101.

Figure 1B:
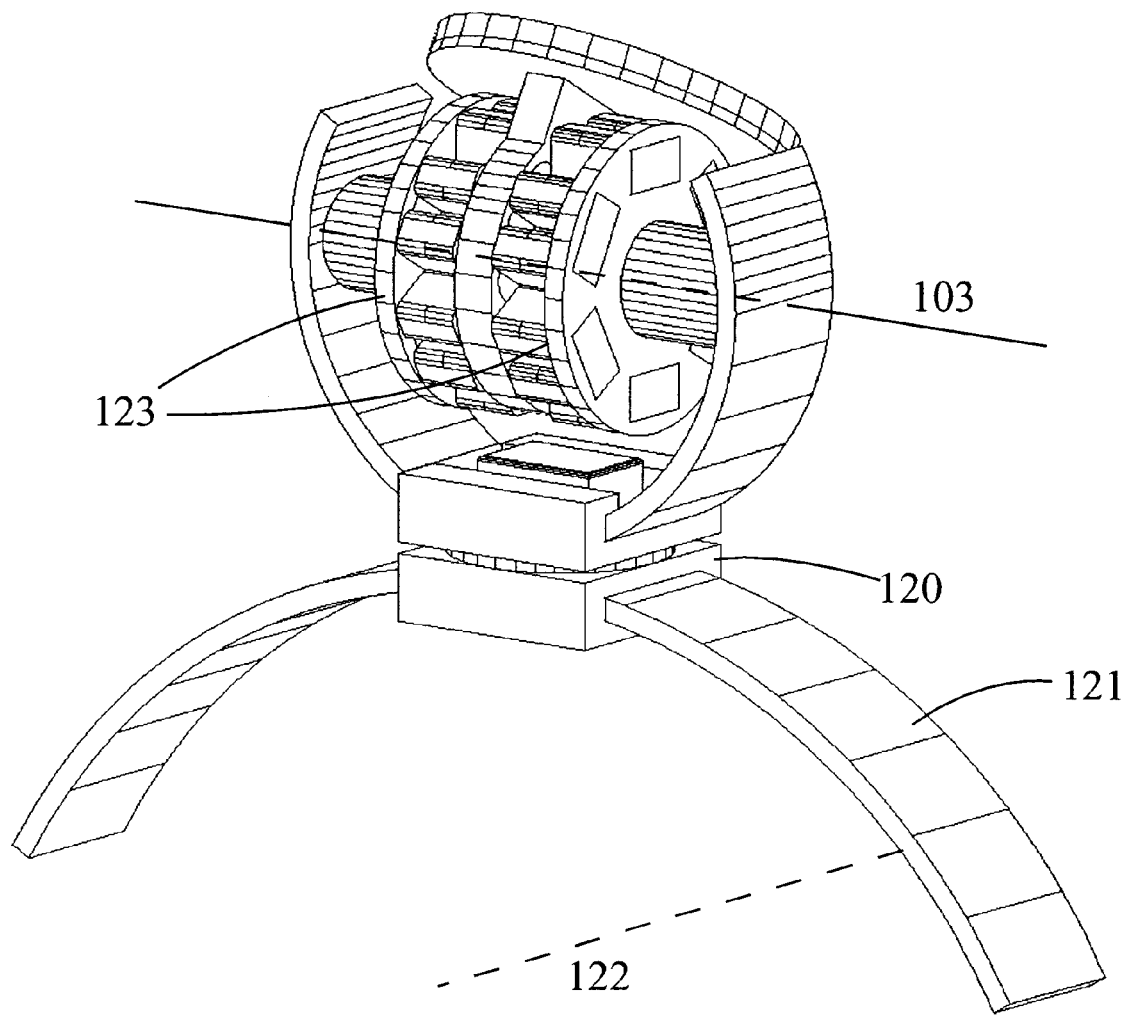
FIG. 1b shows sliding of the fork in a sliding system that provides rotation of the array around an elevation axis normal to the azimuth axis and at a distance from the azimuth axis.

FIG. 1b shows a modification of the embodiment where the sliding system 120 slides along a fork 121, arranged so that the shaft 103 rotates around an axis 122 on the side of the sliding system opposite to the shaft axis 103. An advantage of this sliding system is that the width of the beam scanning area becomes wider at the probe surface, than for the scanning system in FIG. 1a. The scanning system in FIG. 1a, however, produces a small outer dimension of the probe.

The rotor 102 of FIG. 1a contains a set of permanent magnets distributed around the rotor in a sequence with opposite polarities, where in the drawing 3 magnets 108 are visible. Rotation of the rotor 102 causes the magnets to slide between the poles of a set of electromagnets with iron cores 109 with surrounding coils 110. In FIG. 1a, some of the magnets are removed for clarity, the cores 109 are shown without coils for some magnets, while the coils 110 around the cores are shown for other magnets. In FIG. 1b an embodiment of an entire electromagnet system 123 is shown. By controlling the current in the coils according to standard methods for those skilled in the art, a torque is developed on the rotor that causes the transducer array to rotate around the shaft axis 103.

For this particular embodiment, an optical reflectance grating 111 in FIG. 1a is mounted around the rotor periphery. The grating is illuminated with a light emitting diode contained in the unit 112. The light reflected from the grating is picked up with two light detection diodes tin the unit 112 that are offset a distance. By monitoring the signals from the two detector diodes one can both observe the direction of movement of the rotor, and its rotation angle measured in steps of ¼ of the angle between the reflection stripes of the position grating 111, according to well known principles.

Figure 2:
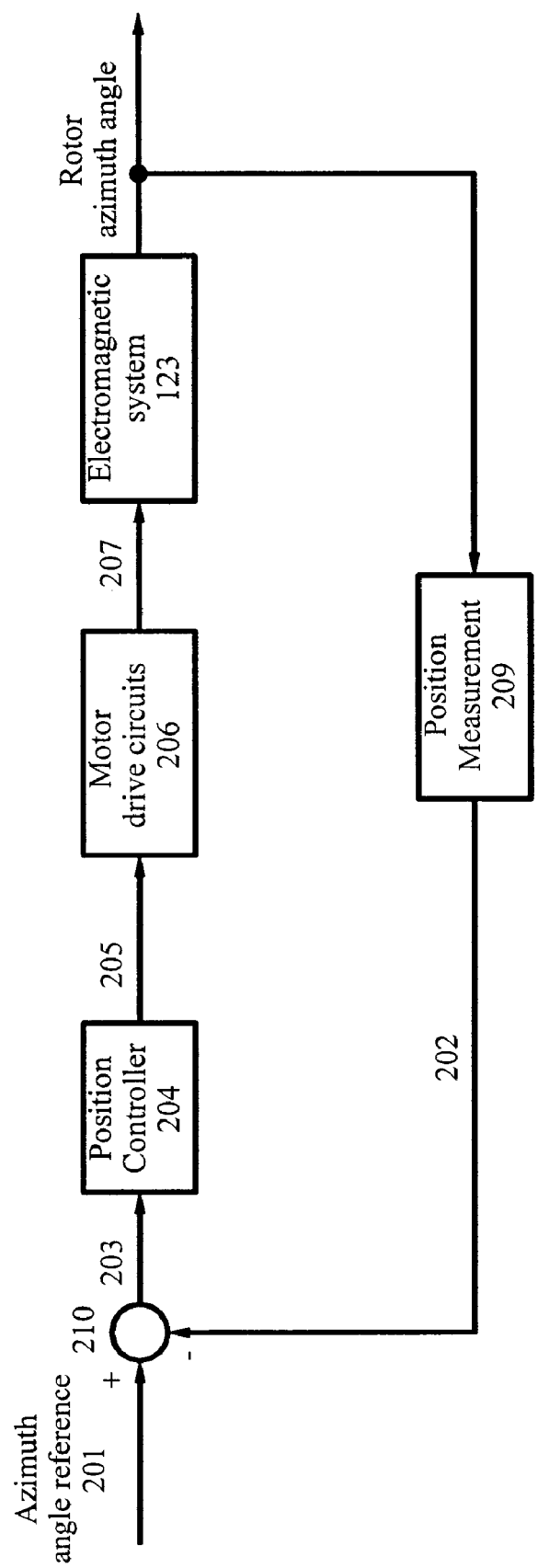
FIG. 2 shows an example of a control system for driving the rotation of the transducer around the azimuth axis to follow an azimuth reference signal.

The system hence provides both a motor to produce a torque on the shaft 103 and a position system to measure the direction and angular rotation of the transducer array around the shaft axis. The motor and the position measurement system can hence be connected in a feed-back control system for rotation of the transducer array around the shaft 103 under feed-back control. This allows precise direction steering of the array around the shaft axis, for example with an electronic control system as shown in FIG. 2.

In this Figure, the azimuth angle of the transducer array is measured in a unit 209, which includes 111 and 112 of FIG. 1a, producing a measured azimuth angle signal 202. The measured azimuth angle signal 202 is compared with an azimuth angle reference signal 201 in the unit 210 that produces the angular position error 203 as the difference between the reference and the measured position. The position error signal is fed to a controller unit 204 that provides inputs 205 to the motor drive unit 206 that provides a set of electric drive signals 207 for the motor electromagnetic system 123 of FIG. 1b. The control system hence drives the rotor azimuth angle to follow the azimuth angle reference.

Figure 3:
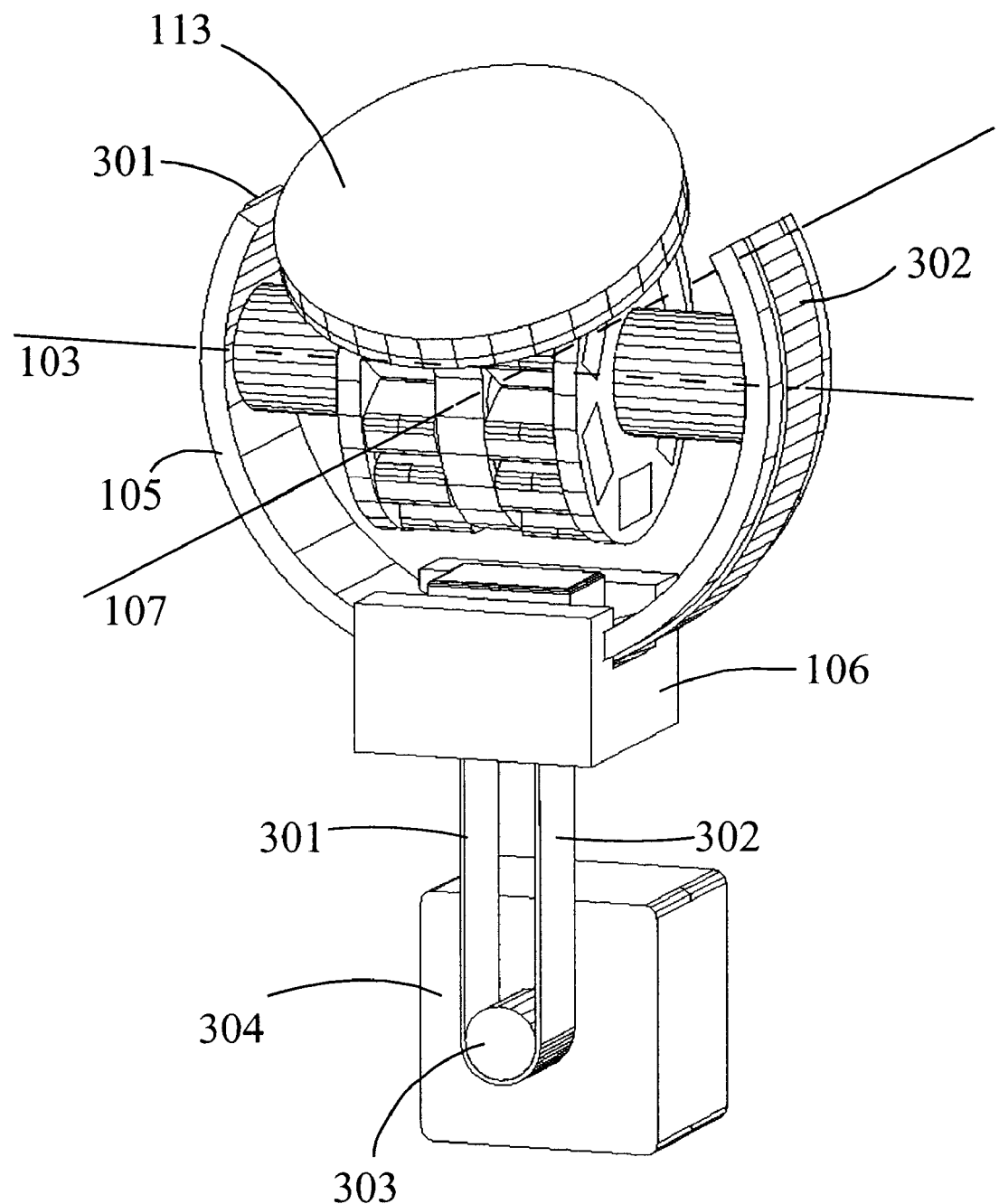
FIG. 3 shows a system with flexible bands thread around a pulley wheel attached to an electric motor for moving the fork in a sliding system.

To scan the beam in the elevation direction in FIG. 1a, the fork is moved in the sliding system 106. A system to control such sliding according to the embodiment, is shown in FIG. 3. Two flexible bands 301 and 302 are attached to the fork 105, so that when one of the bands are pulled, the fork slides in the sliding system 106. This sliding produces a movement of the azimuth rotation axis of the shaft 103, where in this particular embodiment the shaft rotates around an elevation axis 107 normal to the shaft axis. The combined rotation around the azimuth shaft axis 103 and the elevation fork axis 107, produces a 3D sector scanning of the beam in both the azimuth and the elevation directions. In this embodiment, the two flexible bands 301 and 302 are connected together in a loop around a pulley wheel 303 connected to a rotating electrical motor 304. Angle controlled rotation of the motor 304, for example by a control system similar to that in FIG. 2, causes a controlled rotation of the transducer around the elevation axis 107.

Figure 1C:
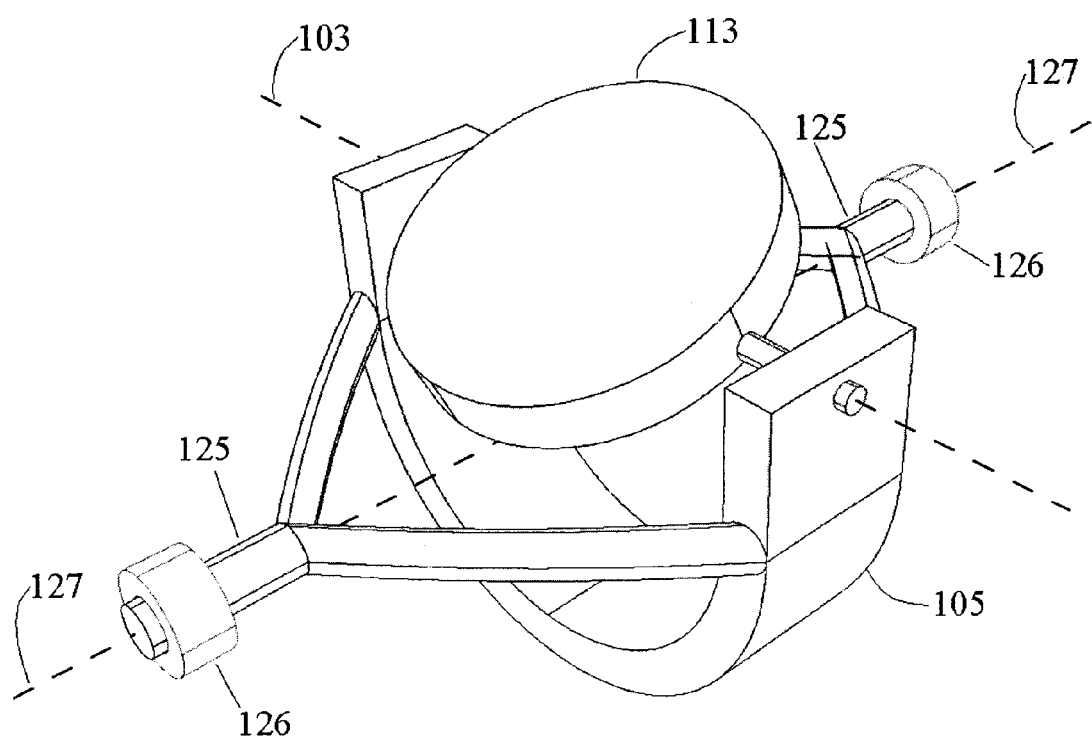
FIG. 1c shows rotation of the fork around a $2^{nd}$ shaft that provides rotation of the array around an elevation axis.

A third method according the invention of moving the azimuth rotation axis 103 is illustrated in FIG. 1c, where the fork 105 is connected to a $2^{nd}$ shaft 125 that can rotate in the bearing system 126 to rotate the array 113 around both the elevation axis 127 and the azimuth axis 103.

Figure 1D:
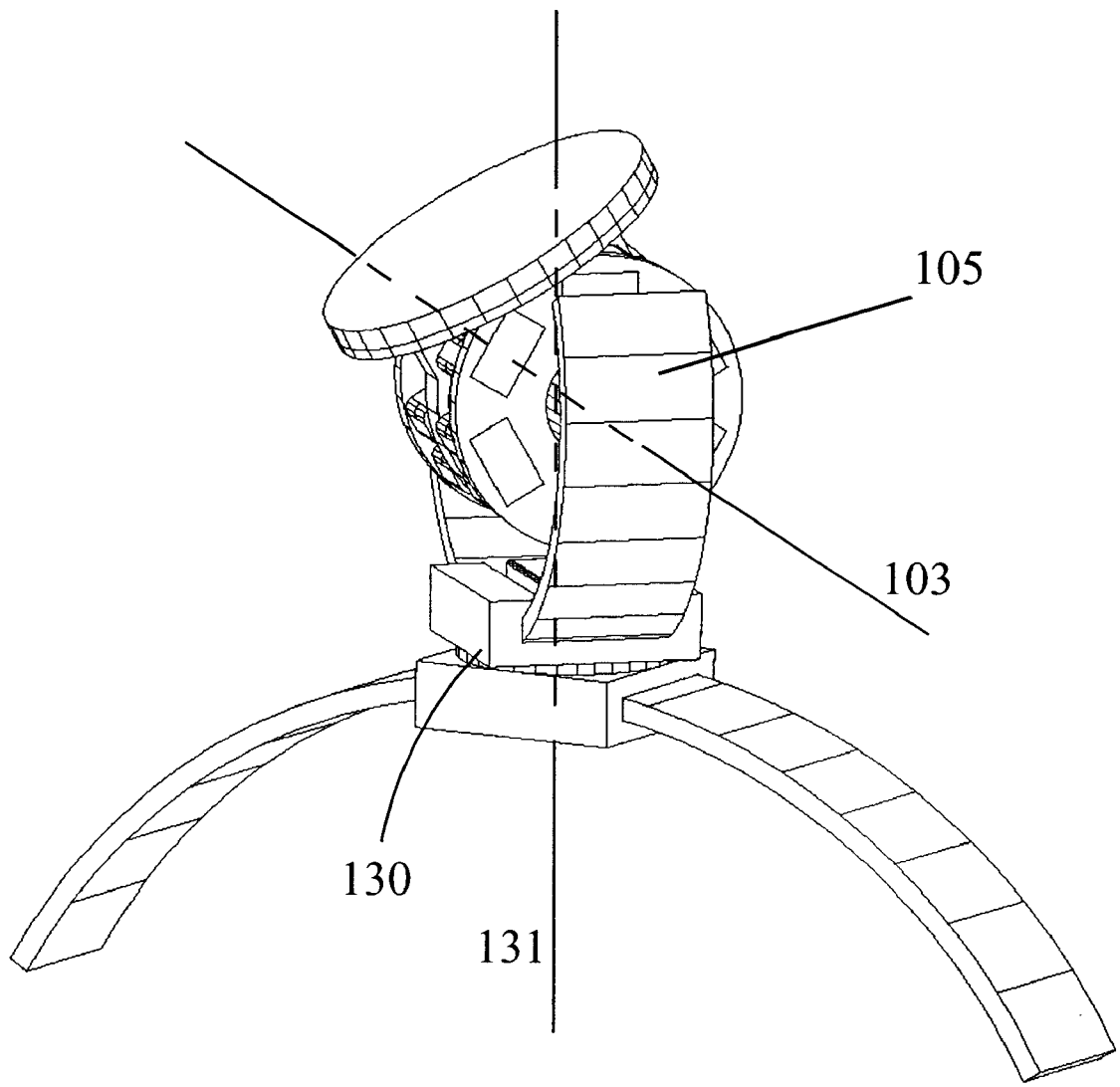
FIG. 1d shows combined rotation of the fork around a roll axis.

A fourth method according the invention of moving the azimuth rotation axis 103 is illustrated in FIG. 1d, where the fork 105 is mounted in a shaft-bearing system 130 that allows the fork and hence the azimuth axis 103 to rotate around the roll axis 131, normal to the azimuth axis. Combined rotation around the azimuth axis 103 and the roll axis 131 produces a 3D scanning of the beam direction. Rotation around the roll axis 131 can be obtained by an electric motor with direct coupling, coupling through a gear or through a set of pulleys.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. An ultrasound probe for scanning the direction and focus of an ultrasound beam containing ultrasound waves in 3D space, said ultrasound probe comprising:

an ultrasound transducer array having a front face, said transducer array emitting an ultrasound transmit beam and receiving incoming ultrasound waves through said front face;

a first shaft, rotatable about a longitudinal axis, said first shaft being disposed to carry said transducer array and providing for rotation of said transducer array about said longitudinal axis;

a first bearing system in which said first shaft is mounted to permit rotation of said first shaft about said longitudinal axis;

a fork in which said bearing system is mounted, said fork being moveable so as to change an angular position of said first shaft in a direction transverse to said longitudinal axis;

a first electric motor having a rotor and a stator, said transducer array being mounted on one of said rotor and said stator, and the other of said rotor and said stator being connected to said fork to rotate said transducer array about said longitudinal axis of said first shaft; and an angular position sensor element connected to said transducer array, for sensing a rotation angle of said transducer array and said ultrasound beam with respect to said longitudinal axis;

whereby rotating said transducer array about said longitudinal axis of said first shaft and changing said angular position of said longitudinal shaft within said fork permits the orientation of said ultrasound beam in two different transverse directions and thereby also permits directing said ultrasound transmit beam in any direction within a region of 3D space being scanned.

2. The ultrasound probe according to claim 1:

wherein said bearing system includes two bearings each attached to said first shaft at opposing ends thereof and each mounted within said fork; and wherein said first motor, said transducer array, and said sensor element are positioned on said first shaft between said two bearings.

3. The ultrasound probe according claim 1, wherein said transducer array is annular.

4. The ultrasound probe according to claim 1, wherein said fork is rotatably moveable around a second shaft, which is mounted in a bearing.

5. The ultrasound probe according to claim 1, further comprising a sliding system in which said fork is slideably moveable.

6. The ultrasound probe according to claim 1, further comprising a second electric motor coupled to said fork for changing said angular position of said first shaft, and whereby said first and second electric motors direct said transducer array in any direction within said region of 3D space.

7. The ultrasound probe according to claim 6, wherein said fork has a circular shape and is slideably moveable in said first sliding system such that sliding of said fork in said first sliding system rotates said first shaft around an axis of said first sliding system that is on the same side of said first sliding system as said first shaft, said axis being normal to said first shaft.

8. The ultrasound probe according to claim 6, wherein said fork has a circular shape and is slideably moveable in said first sliding system such that sliding of said fork in said first sliding system rotates said first shaft around an axis of said first sliding system that is on an opposite side of said first sliding system as said first shaft, and is normal to said first shaft.

9. The ultrasound probe according to claim 6, wherein said fork is slideably moveable in said first sliding system such that sliding of said fork in said first sliding system laterally displaces said first shaft.

10. The ultrasound probe according to claim 1, where said fork is operationally connected to at least one flexible band, said at least one flexible band being capable of controlling movement of said fork by exerting a force on said at least one flexible band.

11. The ultrasound probe according to claim 10, wherein a first side of said fork is attached to a first flexible band, and a second opposing side of said fork is attached to a spring system, said fork being movable in one of a first direction and a second direction through a combined action of said spring system and the exertion of a force on said flexible first band, such that exerting said force on said first flexible band moves said fork in said first direction and said spring system pulls said fork in said second direction, opposite to said first direction, when said force on said flexible band is removed.

12. The ultrasound probe according to claim 10, where a first side of said fork is attached to a first flexible band and a second side of said fork is attached to a second flexible band, such that bi-directional movement of said fork is obtained by selectively exerting a force on one of said first and second bands.

13. The ultrasound probe according to claim 10, further comprising a second electric motor coupled to said at least one flexible band to exert said force on said at least one flexible band.

14. The ultrasound probe according to claim 13, further comprising:

a position measurement unit, for measuring an angular position of said first shaft and a position of said fork, said position measurement unit generating position signals; and a feed-back controller that provides drive signals for said first and second electric motors in response to said positioning signals, to steer the direction of said ultrasound beam so that said measured angular position of said first shaft and said position of said fork direct said ultrasound beam in a predetermined direction within said region of 3D space.

15. The ultrasound probe according to claim 10, further comprising:

a sliding system;

a second bearing system movably attached to said sliding system and capable of changing at least one of a position and a direction of said second bearing system within said sliding system; and a second electric motor connected to said sliding system to change said at least one of said position and said direction of said second bearing system.

* * * * *